US009056872B2

(12) United States Patent
Trippé-Allard et al.

(10) Patent No.: US 9,056,872 B2
(45) Date of Patent: Jun. 16, 2015

(54) ORGANIC COMPOUNDS, PROCESS FOR PREPARING SAME AND USES IN ELECTRONICS

(75) Inventors: Gaëlle Trippé-Allard, Massy (FR); Jean-Christophe Lacroix, La Varenne Saint Hilaire (FR)

(73) Assignees: UNIVERSITE PARIS DIDEROT—PARIS 7 (FR); CENTRE NATIONAL DE LA RECHERCHE SCIENTIFIQUE (CNRS) (FR)

( * ) Notice: Subject to any disclaimer, the term of this patent is extended or adjusted under 35 U.S.C. 154(b) by 0 days.

(21) Appl. No.: 13/698,688

(22) PCT Filed: May 19, 2011

(86) PCT No.: PCT/FR2011/051140
§ 371 (c)(1),
(2), (4) Date: Nov. 19, 2012

(87) PCT Pub. No.: WO2011/144873
PCT Pub. Date: Nov. 24, 2011

(65) Prior Publication Data
US 2013/0079529 A1   Mar. 28, 2013

(30) Foreign Application Priority Data
May 19, 2010   (FR) ..................... 10 53856

(51) Int. Cl.
*H05B 33/12* (2006.01)
*H01J 17/00* (2006.01)
*C07D 495/04* (2006.01)
*H05B 33/14* (2006.01)

(52) U.S. Cl.
CPC .............. *C07D 495/04* (2013.01); *H05B 33/14* (2013.01)

(58) Field of Classification Search
CPC ...................................................... H01B 33/14
USPC .................. 549/50, 43, 59, 68; 428/690, 917; 430/319; 313/504, 506
See application file for complete search history.

(56) References Cited

U.S. PATENT DOCUMENTS

| | | | | |
|---|---|---|---|---|
| 6,130,339 | A | 10/2000 | Tan et al. | 549/50 |
| 6,197,921 | B1 | 3/2001 | Tan et al. | 528/380 |
| 7,186,468 | B2 * | 3/2007 | Iwanaga | 428/690 |
| 2004/0062950 | A1 | 4/2004 | Iwanaga | 428/690 |

FOREIGN PATENT DOCUMENTS

WO   WO 99/66169 A2   12/1999

OTHER PUBLICATIONS

International Search Report and Written Opinion mailed Jan. 20, 2012 in corresponding PCT International Application No. PCT/FR2011/051140.
P. Amaladass et al: "Pd-mediated C—H acylation of EDOT and synthesis of push-pull systems incorporating EDOT", Tetrahedron, vol. 63, No. 41, pp. 10363-10371, Aug. 31, 2007.
Lucia Flamigni, et al., "A Triphenylamine/Bis(terpyridine)Ir$^{III}$ Dyad for the Assembly of Charge-Separation Constructs with Improved Performances," Eur. J. Inorg. Chem., 2007, pp. 5189-5198.
A. Borghese, et al., "Direct C-H arylation of 3-methoxythiophene Catalyzed by Pd. Application to a More Efficient Synthesis of π-alkoxy-oligothiophene Derivatives," Tetrahedron Letters, vol. 47, 2006, pp. 9249-9252.
Mathieu Turbiez, et al., "Oligothienylenevinylenes Incorporating 3,4-ethylenedioxythiophene (EDOT) Units," Tetrahedron, vol. 61, No. 12, Mar. 21, 2005, pp. 3045-3053.
Gregory a. Sotzing, et al., "Poly(3,4-ethylenedioxythiophene) (PEDOT) Prepared via Electrochemical Polymerization of EDOT, 2,2'-Bis(3,4-ethylenedioxythiophene) (BiEDOT), and Their TMS Derivatives," Advanced Materials, vol. 9, No. 10, 1997, pp. 795-798.
Michael Frigoli, et al., "Synthesis of New Thiophene-Substituted 3,3-Diphenyl-3H-naphthol[2,1-b]pyrans by Cross-Coupling Reactions, Precursors of Photomodulated Materials," Eur. J. Org. Chem., 2003, pp. 2799-2812.
European Office Action dated Feb. 11, 2015 in corresponding European Patent Application No. 11 727 236.9 (with English translation of comments on the inventive step (4. Activité inventive)(7 pages).
Claire Faye, et al., "Tunable Electrochemical Switches Based on Ultrathin Organic Films," J. Am. Chem. Soc. 2007, 129, pp. 1890-1891.
Verena Stockhausen, et al. "Grafting Oligothiophenes on Surfaces by Diazonium Electroreduction: A Step Toward Ultrathin Junction With Well-Defined Metal/Oligomer Interface," J. Am. Chem. Soc. 2009, 131, pp. 14920-14927.

* cited by examiner

*Primary Examiner* — Andrew D Kosar
*Assistant Examiner* — Raymond Covington
(74) *Attorney, Agent, or Firm* — Ostrolenk Faber LLP

(57) ABSTRACT

The present disclosure relates to novel organic compounds, to the processes for preparing same and to the uses thereof, firstly in the electronics field, in particular in the fields referred to as plastic electronics and molecular electronics, and, secondly, in the coatings field, in particular in the fields of adhesion primers and intelligent coatings. The disclosure also relates to a material comprising a novel compound according to the invention.

23 Claims, No Drawings

ORGANIC COMPOUNDS, PROCESS FOR PREPARING SAME AND USES IN ELECTRONICS

CROSS-REFERENCE TO RELATED APPLICATIONS

The present application is a 35 U.S.C. §371 National Phase conversion of PCT/FR2011/051140, filed May 19, 2011, which claims benefit of French Application No. 1053856, filed May 19, 2010, the disclosures of which are incorporated herein by reference. The PCT International Application was published in the French language.

BACKGROUND OF THE INVENTION

1. Technical Field

The present invention relates to novel organic compounds, to their processes of preparation and to their uses, on the one hand in the field of electronics, in particular in the fields of "plastic electronics" and "molecular electronics" and, on the other hand, in the field of coatings, in particular in the fields of adhesive primers and intelligent coatings.

The invention also relates to a material comprising a novel compound according to the invention.

In the description below, the references between square brackets [ ] refer to the list of references which is presented at the end of the text.

2. Related Art

For several years, research targeted at developing novel organic compounds, in the form of a crystal or of a polymer, for example, which show similar properties to inorganic compounds has continued to expand. These properties are conduction by electrons and holes, and the presence of a forbidden band. Furthermore, research targeted at developing novel functional coatings is also very active. By virtue of their elasticity, their lightness, their strength and their plasticity, organic molecules are of great interest due in particular to the extent of their fields of application in electronics or also as functional coatings.

Unlike materials based on inorganic compounds (inorganic materials), such as silicon, for example, materials based on organic molecules (organic materials) exhibit the advantage of being able to be deposited and/or grafted, in the form of thin films or layers, by relatively inexpensive techniques, on flexible and light substrates which are conducting or insulating.

Furthermore, like inorganic materials, organic materials can be doped, that is to say the density of the electrons (N doping) or of the holes (P doping) can be increased therein.

The immobilization of organic compounds, for example in the form of a polymer, on insulating, metal, semiconducting or carbon-based substrates makes it possible to develop novel interfaces for applications which can range from the manufacture of molecular or plastic electronic devices, biosensor systems, corrosion-resistant coatings, to intelligent coatings.

The formation of thin films or layers resulting from the grafting or deposition of organic molecules or polymers at the surface of the substrates makes it possible both to maintain the properties of the substrates and to confer, at the surface of the material, novel and distinct properties. One of the particular advantageous properties is in particular the ability to switch between different electrical conduction states. The nature of the organic compounds can determine the electric potential at which the layer switches.

At the current time, the existing organic compounds capable of forming deposited or grafted layers at the surface of the substrates are not entirely satisfactory for at least one of the following reasons:

- they are not suitable for all types of substrates in the sense that they cannot form thin films or layers by grafting or deposition on all types of substrate;
- the layer(s) formed are not always homogeneous (in particular in thickness), which can affect the quality and the properties of the layer and of the substrate on which it is deposited or grafted and of the interface between the substrate and the layer or layers and thus the quality of the material or devices using these layers;
- the number of layer(s) deposited or grafted cannot be adjusted, which can result in films which are either too thin or too thick, and can thus affect the quality and the properties of this layer, of the substrate on which said layer is deposited or grafted and of the interface and consequently the quality of the material or devices using these layers;
- the nature of the interface between the substrate and the layer is not always controlled, which can result in layers which do not adhere strongly and/or in an interface exhibiting hole- or electron-injection barriers which are insufficient for the uses targeted, and can affect the quality of the devices using these layers;
- the layer or layers formed often exhibit defects of micronic or subnanometric size which are harmful to the quality of the layer, of the substrate on which it is deposited or grafted and of the interface and consequently the quality of the material or devices using these layers;
- although grafted to the substrate, the layer or layers formed are not always electroactive, which can result in properties which cannot be adjusted via an electrochemical or electrical stimulus (electron- or hole-injection, for example) and can thus affect the quality of the devices using these layers;
- although grafted to the substrate, the electroactive layer or layers formed do not always switch between two states having different conduction properties;
- the electroactive layer or layers formed do not always switch between two states having different conduction properties at the electric or electrochemical potential desired, which can affect the quality of the devices using these layers;
- the use of the organic compounds and/or the formation of organic polymers can present technical problems, in particular in terms of reproducibility and/or operating on the industrial scale.

The need to have available novel organic compounds capable of forming one or more electroactive layers which can switch between an insulating state and a conducting state at the surface of various types of substrates, overcoming the failings, disadvantages and obstacles of the state of the art, remains topical.

There thus exists a real need to have available novel organic compounds which are compatible with any type of substrate and which are capable of forming one or more layer(s) at their surface.

There also exists a real need to provide novel organic compounds, the use of which and/or the formation of polymers of which is easy and reproducible, can be carried out industrially and is economically advantageous.

DESCRIPTION OF EMBODIMENTS

It is a specific aim of the present invention to meet these needs by providing compounds of formula (I):

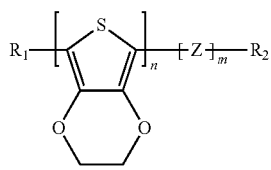

in which:
R₁ represents a hydrogen atom, a halogen atom, a hydroxyl group, a $C_1$-$C_4$ alkoxy group, a —$COOR_3$ group, a —$COR_3$ group, an —$SR_3$ group, an —$SeR_3$ group, an —$Si(OR)_3$ group, an —$NR_3R_4$ group, a —C≡N group, an —$N_3$ group, a —C≡C—H group, a heterocycle chosen from the group consisting of pyrrole, furan, phosphole, thiophene, tetrathiafulvalene, selenophene, imidazole, oxazole, thiazole, triazole, pyrazole, pyridine, bipyridine, terpyridine, phenanthroline, pyrazine, pyridazine and pyrimidine, ferrocene, cobaltocene, a polyethylene group of formula —(—O—$CH_2$—$CH_2$—)$_p$—, a $C_1$-$C_{10}$ alkyl group and a phenyl group, said polyethylene, alkyl, phenyl and heterocycle groups being optionally substituted by one or more groups chosen from the group consisting of:
a —$COOR_3$ group, a —$COR_3$ group, a hydroxyl group, a $C_1$-$C_4$ alkoxy group and a —$CONR_3R_4$ group;
R₂ represents an amino (—$NH_2$) group, a diazo ($N_2^+$) group, an aniline group, a phenyl group substituted by a diazo ($N_2^+$) group, an —$NO_2$ group or a phenyl group substituted by an —$NO_2$ group; optionally substituted by one or more groups chosen from a $C_1$-$C_4$ alkyl group, a —$COOR_3$ group, a —$COR_3$ group, a hydroxyl group, a $C_1$-$C_4$ alkoxy group, a —$CONR_3R_4$ group, an —$NO_2$ group or an —$NR_3R_4$ group;
Z represents thiophene, optionally substituted by one or more groups chosen from the group consisting of:
a $C_1$-$C_{10}$ alkyl group, a carboxyl group, a —$COOR_3$ group, a hydroxyl group or a $C_1$-$C_4$ alkoxy group;
R₃ and R₄ represent, independently of one another, a hydrogen atom, a $C_1$-$C_6$ alkyl group or a phenyl group;
n=1, 2, 3, 4 or 5;
m=0, 1, 2 or 3;
p=0, 1, 2, 3, 4 or 5;
it being understood that, when R₁ represents a hydrogen atom and m=0, then n is other than 1.

The compounds of formula (I) have the advantage of being compatible with any type of substrate and can form one or more layer(s) at their surface. The formation of said layer(s) at the surface of the substrate can be carried out by deposition of or by grafting the compounds of formula (I). Within the meaning of the invention, the term deposition is understood to mean the formation of one or more layers at the surface of a substrate by oxidation of the compounds of formula (I). The term grafting is understood to mean the formation of one or more layers at the surface of a substrate by reduction of said compounds of formula (I), namely: attachment of the compounds to the substrate in an essentially covalent way.

Thus, the compounds of formula (I) can adhere to the substrates by grafting. Grafting can be carried out by means of any type of bond which makes possible good adhesion of said compounds to the substrate, for example by means of strong bonds.

The term "alkyl" is understood to mean, within the meaning of the present invention, a saturated and linear, branched or cyclic carbon-based group which is optionally substituted and which comprises from 1 to 10 carbon atoms, for example from 1 to 6 carbon atoms, for example from 1 to 4 carbon atoms. Mention may be made, by way of indication, of the methyl, ethyl, propyl, isopropyl, n-butyl, sec-butyl, isobutyl, tert-butyl, cyclobutyl, pentyl (or amyl), sec-pentyl, isopentyl, neopentyl, hexyl, isohexyl, tert-hexyl, neohexyl, heptyl, octyl, nonyl or decyl groups and their branched and/or cyclic isomers.

The term "heterocycle" is understood to mean, within the meaning of the present invention, a system comprising at least one aromatic ring or one saturated or unsaturated ring comprising at least one heteroatom chosen from the group consisting of sulfur, oxygen, nitrogen and phosphorus. In the context of the invention, the heterocycles can comprise from 3 to 20 carbon atoms. The heterocycles can be substituted. Mention may be made, as examples of heterocycles, of pyrrolidine, pyrazoline, pyrazolidine, imidazole, imidazolidine, piperidine, piperazine, oxazolidine, isoxazolidine, morpholine, thiazole, thiazolidine, isothiazolidine, tetrahydrofuran, pyridine, bipyridine, terpyridine, pyridazine, pyrazine, pyrimidine, pyrrole, pyrazole, triazole, imidazoline, thiazoline, oxazole, oxazoline, isooxazoline, thiadiazoline, oxadiazoline, thiophene, furan, quinoline, isoquinoline, benzopyrrole, benzofuran, benzothiophene, phosphole, tetrathiafulvalene, selenophene, phenanthroline and similar groups.

The term "alkoxy" is understood to mean, within the meaning of the present invention, a saturated and linear, branched or cyclic alkyl group which is optionally substituted and which is bonded to an oxygen atom. For example, an alkoxy radical can be a methoxy, ethoxy, propoxy, isopropoxy, n-butoxy, tert-butoxy, neopentoxy or n-hexoxy radical or a similar radical.

The term "aryl" group is understood to mean an aromatic hydrocarbon which is optionally substituted. For example, an aryl group can be a phenyl group, a benzyl group, a tolyl group, a xylyl group or vinylbenzene.

Within the meaning of the invention, the halogen atom can be chosen from the group consisting of fluorine, chlorine, bromine and iodine.

The term "substituted" denotes, for example, the replacement of a hydrogen atom in a given structure by a group as defined above. When more than one position can be substituted, the substituents can be the same or different at each position.

In the context of the present invention, the term "to switch" is understood to mean the alternation between the nonconducting (or insulating) reduced state and the conducting oxidized state of the organic compounds according to the invention.

Within the meaning of the invention, the term "polymer" means a sequence of at least two identical or different and natural or synthetic compounds. This sequence can be linear or branched. The term "polymer" encompasses oligomers and homopolymers as well as copolymers.

Within the meaning of the invention, the term "electroactive or electroactivity" denotes a state where an exchange of electrons takes place. More particularly, an electroactive layer denotes a layer capable of alternating between two different conduction states, in particular between the nonconducting (or insulating) reduced state and the conducting oxidized state.

According to a first embodiment of the invention, the compounds of the invention can be of formula (I) in which: R₁ represents a hydrogen atom or thiophene; R₂ represents the amino (—$NH_2$) group or the aniline group; Z represents thiophene; n=1, 2 or 3; m=0 or 1; it being understood that, when R₁ represents a hydrogen atom and m=0, then n is other than 1. The compounds according to the first embodiment are particularly advantageous since they are capable of forming layers or films on substrates by grafting. This makes it possible to obtain a layer exhibiting both the switching nature between an insulating state and a conducting state, and very good adhesiveness on the substrate.

According to a second embodiment, the compounds of the invention can be of formula (I) in which: $R_1$ represents a hydrogen atom or thiophene; $R_2$ represents the aniline group, the phenyl group substituted by the diazo ($N_2^+$) group or the phenyl group substituted by the —$NO_2$ group; Z represents thiophene; n=1, 2 or 3; and m=0 or 1; it being understood that, when $R_1$ represents a hydrogen atom and m=0, then n is other than 1. The compounds according to the second embodiment make it possible to form, either by grafting or by deposition on any type of substrate, thin films or layers having the ability to switch.

According to the invention, it is preferable, when m=0, for n to be other than 1.

According to an advantageous alternative form of the invention, $R_1$ represents a hydrogen atom; $R_2$ represents the aniline group; n=2; and m=0. It thus concerns 2-(4-aminophenyl)-3,4,3',4'-bis(ethylenedioxy)-5,2'-bithiophene (2EB).

According to another advantageous alternative form of the invention, $R_1$ represents thiophene; $R_2$ represents the aniline group; n=1; and m=0. It thus concerns 2-(4-aminophenyl)-3,4-ethylenedioxy-5,2'-bithiophene (TEB).

According to an advantageous alternative form of the invention, $R_1$ represents a hydrogen atom; $R_2$ represents the aniline group; Z represents thiophene; n=1; and m=1. It thus concerns 2-(4-aminophenyl)-3',4'-ethylenedioxy-5,2'-bithiophene (ETB).

According to an advantageous alternative form of the invention, $R_1$ represents a hydrogen atom; $R_2$ represents the aniline group; n=3; and m=0. It thus concerns 2-(4-aminophenyl)-3,4,3',4',3'',4''-ter(ethylenedioxy)-5,2',5',2''-terthiophene (3EB).

Surprisingly, when the thin films or layers are formed from the compounds 2EB, TEB, ETB or 3EB, it is possible to obtain better adhesion to the substrate while retaining the ability to switch between an insulating state and a conducting state.

The compounds according to the invention offer several advantages in comparison with the organic compounds conventionally used. As already indicated, the compounds according to the invention can form one or more layers or films which can be grafted to or deposited on any type of substrate, whether insulating or conducting and rigid or flexible. The thickness of these layers or films can be adjusted according to the nature of the organic compounds and/or according to whether they are deposited or grafted. Thus, the thickness of these layers or films can be, for example, between 1 and 100 nm, for example between 1 and 20 nm, for example between 1 and 5 nm, when it concerns grafting by a reduction reaction of the organic compounds of the invention (reductive route), but can also be between 10 nm and 1000 nm, for example between 1 nm and 10 000 nm, for example between 1 and 1000 nm, for example between 1 and 100 nm, when it concerns deposition by an oxidation reaction of said compounds (oxidative route).

These layers, which advantageously have a homogeneous thickness, have the property of being electroactive and of switching between an insulating state and a conducting state. As indicated, the formation of these layers can take place by the reductive route or by the oxidative route. The bond between the surface of the substrates and the compounds of the invention can be strong in nature (grafting by reduction) or weaker in nature (deposition by oxidation). Whether grafted or deposited, said layers have good adhesion to the surface of the substrate. However, when the formation of the layers takes place by grafting, the adhesion of said layers to the substrates is better. The compounds according to the invention thus make it possible to control the interface between the substrate and the layer or film. In the case of grafting by reduction, the grafted molecules result in films exhibiting an ability to switch between an insulating state and a conducting state which is comparable to that which is observed with known conventional organic compounds obtained by oxidative deposition. However, unlike the organic compounds of the state of the art, the compounds of the invention make it possible to significantly adjust the electric potential window which makes possible this switching while making possible strong grafting to the substrate. The switching potential of these layers can lie, for example, between −0.5 volt and +1 volt, for example between −0.3 volt and +1 volt, for example between 0 volt and +1 volt and between 0 volt and +0.5 volt, versus a calomel electrode.

According to a third embodiment of the invention, the compounds of the invention can be of formula (I) in which: $R_2$ represents the —$NO_2$ group or the phenyl group substituted by the —$NO_2$ group. These compounds can operate not only as plastic electronic compound but also as intermediate compound for 2EB, TEB, ETB and 3EB.

According to a characteristic of the invention, $R_1$ represents a hydrogen atom; $R_2$ represents the —$NO_2$ group or the phenyl group substituted by the —$NO_2$ group; n=2; and m=0.

According to a characteristic of the invention, $R_1$ represents thiophene; $R_2$ represents the —$NO_2$ group or the phenyl group substituted by the —$NO_2$ group; n=1; and m=0.

According to a characteristic of the invention, $R_1$ represents a hydrogen atom; $R_2$ represents the —$NO_2$ group or the phenyl group substituted by the —$NO_2$ group; Z represents thiophene; n=1; and m=1.

According to a characteristic of the invention, $R_1$ represents a hydrogen atom; $R_2$ represents the —$NO_2$ group or the phenyl group substituted by the —$NO_2$ group; n=3; and m=0.

The invention also relates to the processes for the preparation of the compounds according to the invention.

According to a first alternative form, the invention relates to a process for the preparation of a compound of formula (I) in which a halogenated compound of formula (II) is reacted with a compound of formula (III) in the presence of at least one palladium catalyst in order to obtain the compound of formula (I):

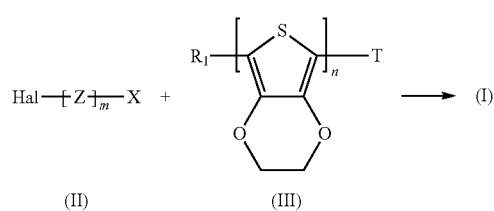

With Z, $R_1$, n and m as defined above;
Hal represents a halogen atom;
T represents a hydrogen atom or a —B(OR')(OR'') group, in which:
R' and R'' represent, independently of one another, a hydrogen atom, a $C_1$-$C_6$ alkyl group or an aryl group chosen from the group consisting of benzyl, phenyl, tolyl and xylyl, or R' and R" together form a 5- or 6-membered ring optionally substituted by one or more $C_1$-$C_4$ alkyl groups;

X represents an —$NO_2$ group or a phenyl group substituted by an —$NO_2$ group.

According to a second alternative form, the invention relates to a process in which a halogenated compound of formula (II) is reacted with a compound of formula (III) in the presence of at least one palladium catalyst in order to obtain the compound of formula (IV), which compound (IV) provides the compound (I) after reduction:

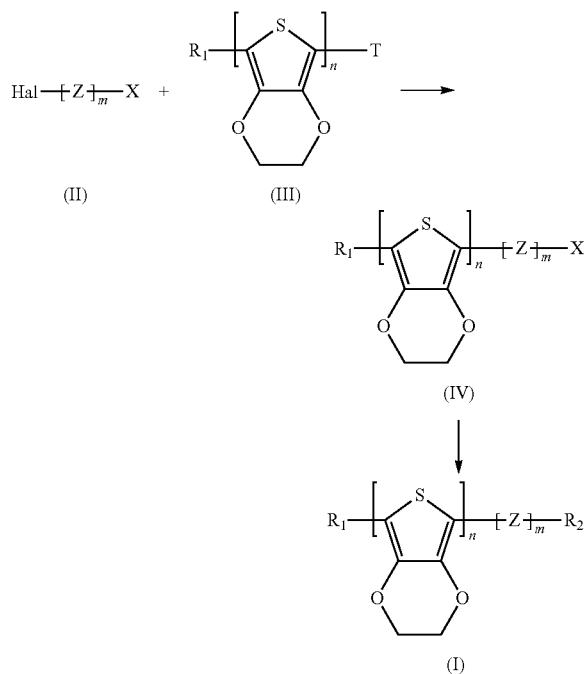

with Z, $R_1$, n and m as defined above;

Hal represents a halogen atom;

T represents a hydrogen atom or a —B(OR')(OR") group, in which:
R' and R" represent, independently of one another, a hydrogen atom, a $C_1$-$C_6$ alkyl group or an aryl group chosen from the group consisting of benzyl, phenyl, tolyl and xylyl, or R' and R" together form a 5- or 6-membered ring optionally substituted by one or more $C_1$-$C_4$ alkyl groups;

X represents an —$NO_2$ group or a phenyl group substituted by an —$NO_2$ group, it being understood that, when X is the —$NO_2$ group, $R_2$ represents an amino (—$NH_2$) group and, when X is the phenyl group substituted by an —$NO_2$ group, $R_2$ represents an aniline group.

In both alternative forms, the reaction of the halogenated compound (II) with the compound of formula (III) can be carried out in the presence of a palladium (Pd) catalyst.

The palladium catalyst can be chosen from the group consisting, for example, of tetrakis(triphenyl-phosphine)palladium(0), 1,2-bis(diphenylphosphino)ethane]palladium(0), palladium(II) acetate, palladium(II) propionate, palladium (II) chloride, palladium(II) bromide, palladium(II) acetylacetonate, di(benzylidene acetate)palladium(0), palladium-on-charcoal and palladium-on-alumina.

Said reaction can be carried out in a polar solvent or a mixture of polar solvents chosen from the group consisting, for example, of N,N-dimethylformamide (DMF), dimethyl sulfoxide (DMSO), acetonitrile, ethyl acetate, triethylamine, pyridine, diethyl ether, THF, diglyme, triglyme, dichloromethane, chloroform, acetone and butanone.

In both alternative forms, the reaction of the halogenated compound (II) with the compound of formula (III) can also be carried out in an ionic liquid chosen from ionic liquids comprising an imidazolium, such as, for example, 1-n-butyl-3-methylimidazolium tetrafluoroborate.

Said reaction can be carried out in the presence of a base chosen from the group consisting, for example, of sodium carbonate, potassium carbonate, cesium carbonate, sodium hydrogencarbonate, potassium hydrogencarbonate, triethylamine, potassium phosphate, silver oxide, sodium tert-butoxide, potassium tert-butoxide, sodium hydroxide, potassium hydroxide, barium hydroxide, cesium fluoride and sodium ethoxide.

The compound (II) reacts with the compound (III) at a temperature of at least 20° C., for example between 40° C. and 140° C., for example between 60° C. and 120° C.

The duration of said reaction varies according to the compounds of formulae (II) and (III), to the palladium catalyst and to the solvent used. It can range from a few minutes to several days. It can range, for example, from 30 minutes to 5 days, for example from 1 hour to 3 days.

In the first alternative form, the compound (I) is obtained on conclusion of the reaction of the compound (II) with the compound (III) and can be used as is or after purification by known methods.

In the second alternative form, the compound of formula (IV) is obtained on conclusion of the reaction between the compounds of formulae (II) and (III). The compound (I) can then be obtained after reduction of said compound of formula (IV).

The reduction of the compound of formula (IV) can be a hydrogenation reaction. The hydrogenation catalyst is advantageously chosen from palladium, rhodium or nickel catalysts, such as, for example, the Lindlar catalyst, palladium-on-charcoal, palladium-on-calcium carbonate, palladium-on-alumina, palladium hydroxide-on-charcoal, palladium(II) acetate, palladium(II) propionate, palladium(II) chloride, palladium bromide, the Wilkinson catalyst and Raney nickel.

The reduction can also be carried out using a hydride. The hydride can be a hydride chosen from the group consisting of $AlH_3/AlCl_3$, sodium dihydro(trithio)borate ($NaBH_2S_3$) and $NaBH_4$ catalyzed by $NiCl_2(PPh_3)_2$ or $CoCl_2$.

The reduction can also be carried out by the action of a metal in an acidic medium. The metal can be zinc, tin or iron. The acid can, for example, be sulfuric acid, hydrochloric acid or nitric acid.

The reduction of the compound of formula (IV) can also be carried out by the action of hydrazine in the presence of a catalyst. The catalyst can advantageously be chosen from catalysts comprising palladium, nickel, iron, zinc or carbon.

Still in the second alternative form, the compound (I) can be obtained after reduction of said compound of formula (IV), for example, by the action of the triirondodecacarbonyl complex [$Fe_3(CO)_{12}$] in an alcoholic medium. The alcoholic medium can be an alcohol or a mixture of alcohols chosen, for example, from methanol, ethanol or isopropanol.

The reduction of said compound of formula (IV) can also be carried out by the action of sulfides. The sulfide can be chosen from sodium hydrosulfide, ammonium sulfide or polydisulfide.

The reduction can in addition be carried out electrochemically in an acidic medium or in a micellar medium; among the surfactants used can be anionic, cationic or neutral in nature.

The reduction reaction of the compound of formula (IV) to result in the compound (I) can be carried out in a suitable solvent or a mixture of suitable solvents chosen from the group consisting, for example, of water, hydrazine, methanol, ethanol, isopropanol, methanoic acid, acetic acid, THF, dichloromethane, chloroform, carbon tetrachloride, N,N-dimethylformamide (DMF), ethyl acetate, benzene, toluene and dioxane.

The reduction reaction is advantageously carried out at the reflux temperature of the solvent or mixture of solvents.

The duration of the reduction reaction can vary and can range, for example, from 30 minutes to 6 hours.

The compound of formula (I) obtained on conclusion of the reduction can be used as is or can be purified by known purification processes.

The halogenated compounds of formula (II) can be prepared by any suitable halogenation process which makes possible the halogenation of a compound of formula (V):

(V)

in which Z, m and X are as defined above.

The halogenation reaction can be carried out by the action of a halogenating agent chosen from the group consisting, for example, of N-chlorosuccinimide, N-bromosuccinimide, N-iodosuccinimide, chlorine, bromine, iodine, sulfuryl chloride, hypochlorous acid, hydrobromic acid, magnesium bromide and magnesium iodide.

The halogenation reaction can be carried out in the presence of a metal chosen from the group consisting, for example, of zinc, mercury oxide and mercury acetate.

The boronic esters of formula (VIII) correspond to the compounds of formula (III) in which T represents a —B(OR')(OR") group. When said boronic esters of formula (VIII) are not commercially available, they can be prepared, for example, by a process in which a compound of formula (VI) is reacted with a borate of formula (VII):

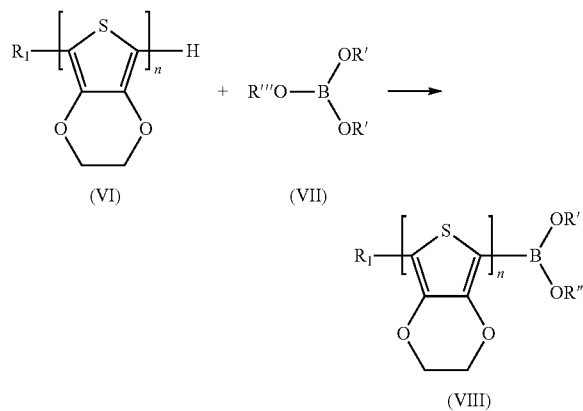

in which $R_1$ and n are as defined above;

R''' represents a hydrogen atom, a $C_1$-$C_6$ alkyl group or an aryl group chosen from the group consisting of benzyl, phenyl, tolyl and xylyl;

R' and R" represent, independently of one another, a hydrogen atom, a $C_1$-$C_6$ alkyl group or an aryl group chosen from the group consisting of benzyl, phenyl, tolyl and xylyl, or R' and R" together form a 5- or 6-membered ring optionally substituted by one or more $C_1$-$C_4$ alkyl groups.

The reaction between the compounds of formulae (VI) and (VII) can be carried out at a temperature which can range from −85° C. to 25° C.

The duration of this reaction can be between 30 minutes and 5 hours.

The reaction between a compound of formula (VI) and a borate of formula (VII) can be carried out in a polar solvent or a mixture of polar solvents chosen from water, N,N-dimethylformamide (DMF), dimethyl sulfoxide (DMSO), N-methylpyrrolidinone, ethanol, propanol, isopropanol, acetonitrile, ethyl acetate, diethyl ether, THF, dioxane, anisole, ethylene glycol dimethyl ether, diglyme, triglyme, dichloromethane, chloroform, acetone or butanone.

Once prepared, the organic compounds of formula (I) are capable of forming deposited or grafted layers at the surface of the substrates by reduction or oxidation. The reduction or the oxidation can be carried out electrochemically or by chemical reactions. In the latter case, any oxidizing agent or any reducing agent having a standard redox potential respectively greater than or less than the standard redox potential of the compound of formula (I) can be used.

The depositing or grafting can be carried out in a polar solvent or in a mixture of solvents chosen from the group consisting, for example, of water, N,N-dimethylformamide (DMF), dimethyl sulfoxide (DMSO), N-methylpyrrolidinone, ethanol, propanol, isopropanol, acetonitrile, ethyl acetate, diethyl ether, THF, dioxane, anisole, ethylene glycol, dimethyl ether, diglyme, triglyme, dichloromethane, chloroform, acetone and butanone.

The depositing or grafting of the organic compounds of formula (I) at the surface of the substrates can also be carried out in an ionic liquid chosen from ionic liquids comprising imidazolium, such as, for example, 1-n-butyl-3-methylimidazolium tetrafluoroborate.

The reduction or oxidation reactions which make possible the grafting or the deposition of the layers, whether chemical or electrochemical in nature, can be carried out in a micellar medium using surfactants which are anionic, cationic or neutral in nature.

The depositing or the grafting of the layers by oxidation or grafting reactions, whether carried out chemically or electrochemically, can also be carried out in an aqueous medium in the presence of cyclodextrins of variable size added in order to dissolve the organic compounds of formula (I).

The processes for the preparation of the organic compounds of formula (I) and the depositing or grafting of said compounds at the surface of the substrates in the form of one or more layers exhibit the advantage of being easy to carry out, of being reproducible, of being able to be carried out industrially and of being economically advantageous.

A subject matter of the invention is the use of a compound of formula (I) as defined above, as plastic electronics, in molecular electronics. The invention relates in particular to the use of said compound of formula (I) to produce a layer on insulating, semi-conducting and conducting surfaces. In this case, it is preferable for said layer to be formed on a substrate by grafting.

More particularly, the compounds of the invention can be used to produce organic light-emitting diodes, transparent electrodes, organic photovoltaic cells, organic transistors, single-electron transistors, or sensors and biosensors.

The invention also relates to the use of a compound of formula (I) as defined above to produce corrosion-resistant coatings, surfaces having switchable wetting properties, self-lubricating surfaces, electrochromic coatings, intelligent coatings, that is to say coatings having certain properties which can be reversibly switched using the external stimulus, or adhesion primers, that is to say layers which make possible the attachment and the adhesion of a second layer having a variable chemical nature but which would not have been adherent if this second layer had been deposited directly on the substrate.

The invention also applies to the use of a compound of formula (I) as defined above in the field of the storage of energy as electrode materials for batteries, or supercapacitors, which are electrical storage systems which can deliver large amounts of energy in a short period of time, in particular as layers deposited on carbon nanotubes.

Another subject matter of the present invention is a material comprising a compound of formula (I) as defined above.

The materials according to the invention can be prepared by known processes.

The present invention, according to another of its aspects, also relates to an article comprising a compound of formula (I) according to the invention as defined above.

EXAMPLES

Solvents and Reactants

The toluene is distilled, under an argon atmosphere, over sodium; the tetrahydrofuran (THF) is distilled, under an argon atmosphere, over sodium and benzophenone. The other solvents used originate from the supplier VWR.

Nuclear Magnetic Resonance (NMR)

The $^1$H and $^{13}$C spectra are recorded with a Bruker Avance III 300 MHz and 400 MHz apparatus.

The chemical shifts ($\delta$) of the $^1$H NMR and $^{13}$C NMR spectra are calibrated with regard to the reference value of the solvent, as described in the paper by Gottlieb et al., *J. Org. Chem.*, 1997, 62, 7512.

The measurements are carried out at 25° C. in tubes with a diameter of 5 mm. The spectra are recorded in deuterated solvents originating from the supplier Eurisotop. The coupling constants are given in hertz.

Chromatography

Thin layer chromatography (TLC) is carried out on "TLC Silica gel 60F$_{254}$" aluminum plates from Merck. The compounds are visualized under a UV lamp at 254 or 326 nm.

The chromatography columns are produced with a silica gel (Silica gel 60 (40-63 µm) from Merck).

Mass Spectrometry

The mass spectra were recorded on a Finnigan 5890 spectrometer coupled to a DSQ 1 in electron impact mode, in solvents of "Analytical" grade.

Synthesis of Precursors

The 1-(thien-2-yl)-4-nitrobenzene and the 1-(3,4-ethylenedioxythien-2-yl)-4-nitrobenzene were prepared according to the protocols described in the references [1] and [2].

For its part, the biEDOT was synthesized according to the procedure described in the reference [3].

Example 1

General Procedure for the Iodination of the Thiophene Derivatives

Mercury oxide (1.04 equivalents, 8.32 mmol) and iodine (1.02 equivalents, 8.16 mmol) are added to a suspension of a thiophene derivative (8 mmol) in acetic acid (150 ml). The mixture is degassed in an ultrasonic bath for 20 minutes and then stirred overnight. The precipitate is filtered off and then dissolved in dichloromethane. The organic phase is washed successively with a potassium iodide solution, a sodium bicarbonate (NaHCO$_3$) solution and water. After drying over magnesium sulfate, the solvent is evaporated under vacuum. The product is used without additional purification.

1-(5-Iodothien-2-yl)-4-nitrobenzene

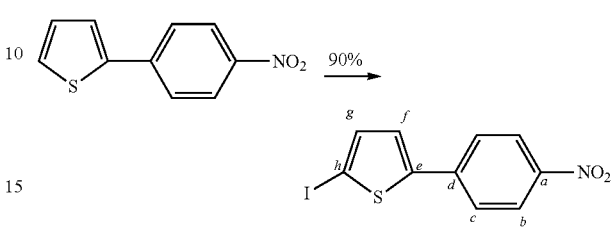

The iodinated thiophene derivative was prepared according to the general procedure for iodination indicated above, with 7 mmol of thiophene derivative.

Yield: 2.10 g; 90%. A yellow powder is obtained.

$^1$H NMR (300 MHz, CDCl$_3$) $\delta$ 7.13 (d, 1H, J=3.6 Hz); 7.30 (d, 1H, J=3.6 Hz); 7.66 (d, 1H, J=8.4 Hz, CH$_c$); 8.23 (d, 1H, J=8.4 Hz, CH$_b$).

$^{13}$C NMR (75 MHz, CDCl$_3$) $\delta$ 76.1 (C$_h$); 124.5 (C$_c$); 125.9 (C$_b$); 127.0 (C$_f$); 138.5 (C$_g$); 139.4 (C$_a$); 146.9 (C$_d$); 147.5 (C$_e$).

MS: M calculated 331; found: [M]$^+$ 331.

1-(5-Iodo-3,4-ethylenedioxythien-2-yl)-4-nitrobenzene

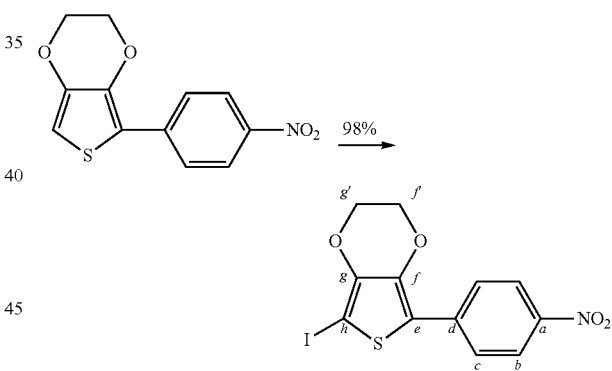

The iodinated EDOT derivative was prepared according to the general procedure for iodination indicated above, starting from 6.57 mmol of 3,4-ethylenedioxythiophene derivative (EDOT).

Yield: 2.52 g; 98%. A yellow powder is obtained.

$^1$H NMR (300 MHz, CDCl$_3$) $\delta$ 4.37 (m, 4H); 7.78 (d, 1H, J=9.2 Hz); 8.21 (d, 1H, J=9.2 Hz).

$^{13}$C NMR (75 MHz, CDCl$_3$) $\delta$ 52.1 (C$_h$); 64.9 and 64.9 (C$_{f'}$ and C$_{g'}$); 120.4 (C$_e$); 124.2 (C$_b$); 125.7 (C$_c$); 139.0 (C$_a$); 139.6 (C$_f$ or C$_g$); 145.0 (C$_f$ or C$_g$); 145.7 (C$_d$).

MS: M calculated 389; found: [M]$^+$ 389.

Example 2

General Procedure for the Synthesis of the Boronic Ester [4]

A solution of the thiophene compound (30 mmol) in distilled THF (100 ml) is cooled to −78° C. with stirring under an argon atmosphere. A 2.5M butyllithium solution (12 ml, 1 equivalent) is added dropwise and the solution obtained is stirred at −78° C. for one hour. Triisopropyl borate (21 ml, 3 equivalents) is added and the reaction mixture is allowed to return to ambient temperature (20° C.). After 2 h 30 min, a solution of pinacol (10.6 g) in THF (30 ml) is added. The reaction mixture is stirred for 30 minutes and the solvent is subsequently evaporated under vacuum. The residue is dissolved in diethyl ether and the solution is washed twice with water and dried over MgSO$_4$. The solvent is evaporated under vacuum. The product is used without additional purification.

4,4,5,5-Tetramethyl-2-(thiophen-2-yl)-1,3,2-dioxaborolane

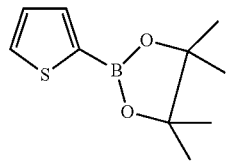

This compound was prepared according to the general procedure above for the synthesis of the boronic ester, starting from 30 mmol of thiophene.

Yield: 5.3 g; 85%. A white powder is obtained.

$^1$H NMR (300 MHz, CDCl$_3$) δ 1.36 (s, 12H, CH$_3$); 7.20 (dd, 1H, J=3.6 and 4.8 Hz, H$_4$); 7.64 (d, 1H, J=4.8 Hz, H$_5$); 7.66 (d, 1H, J=3.6 Hz, H$_3$).

$^{13}$C NMR (75 MHz, CDCl$_3$) δ 24.8 (CH$_3$); 84.1 (C—OB); 128.2 (C$_3$); 132.4 (C$_4$); 137.2 (C$_5$).

MS: M calculated 210; found: [M]$^+$ 210.

2-(2,3-Dihydrothieno[3,4-b][1,4]dioxin-5-yl)-4,4,5,5-tetramethyl-1,3,2-dioxaborolane

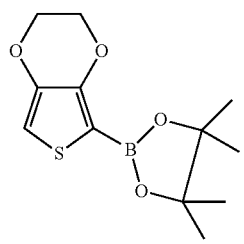 [SMILES: CC1(C)OB(c2scc3c2OCCO3)OC1(C)C]

This compound was prepared according to the general procedure above for the synthesis of the boronic ester, with 50 mmol of EDOT.

Yield: 11.13 g; 85%. A white powder is obtained.

$^1$H NMR (300 MHz, CDCl$_3$) δ 1.34 (s, 12H, CH$_3$); 4.17-4.20 (m, 2H, OCH$_2$); 4.29-4.31 (m, 2H, OCH$_2$); 6.63 (s, 1H, CH$_{edot}$).

$^{13}$C NMR (75 MHz, CDCl$_3$) δ 24.7 (CH$_3$); 64.3 (CH$_2$—O); 65.1 (CH$_2$—O); 83.8 (C—OB); 107.5 (CH$_{edot}$); 142.3 and 149.0 (C$_3$—O and C$_4$—O).

MS: M calculated 268; found: [M]$^+$ 268.

4,4,5,5-Tetramethyl-2-(2,2′,3,3′-tetrahydro-5,5′-bithieno[3,4-b][1,4]dioxin-5-yl)-1,3,2-dioxaborolane

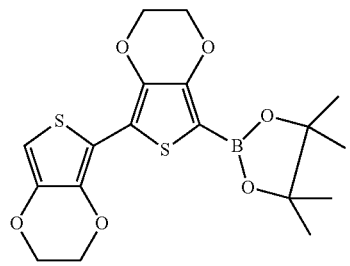 [SMILES: CC1(C)OB(c2sc(-c3scc4c3OCCO4)c3c2OCCO3)OC1(C)C]

This compound was prepared according to the general procedure above for the synthesis of the boronic ester, starting from 10 mmol of bi-EDOT.

Yield: 3.94 g; 93%. A green solid is obtained.

$^1$H NMR (300 MHz, CDCl$_3$) δ 1.28 (s, 12H, CH$_3$); 4.23-4.25 (m, 2H, OCH$_2$); 4.32-4.34 (m, 6H, OCH$_2$); 6.31 (s, 1H).

$^{13}$C NMR (75 MHz, CDCl$_3$) δ 24.5 (CH$_3$); 64.6 (CH$_2$—O); 65.0 (CH$_2$—O); 83.2 (C—OB); 97.5 (CH$_{edot}$); 109.9 (C—S); 137.0 and 141.2 (C—O).

MS: M calculated 408; found: 408.

Example 3

General Procedure for the Suzuki Coupling Reaction [4]

The boronic derivative (2 mmol), the halogenated derivative (2 mmol), sodium carbonate (3 equivalents, 6 mmol) and tetrakis(triphenylphosphine)palladium (Pd$^0$) (5%) are successively introduced into a Schlenk flask containing 25 ml of N,N-dimethylformamide (DMF). The reaction mixture is heated at 110° C. for from 2 to 3 days. After cooling to ambient temperature (20° C.), the solvent is evaporated under vacuum.

The brown residue is dissolved in dichloromethane and the solution is washed twice with water, dried over MgSO$_4$ and concentrated. The crude product is purified by silica gel chromatography.

2-(4-Nitrophenyl)-3, 4-ethylenedioxythiophene

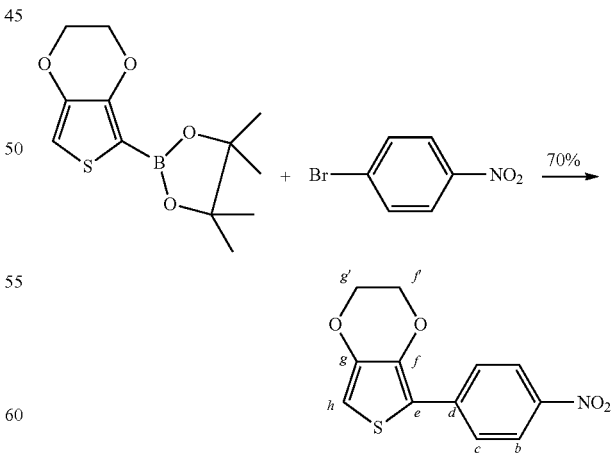

The nitrophenyl-EDOT compound was prepared by the procedure indicated above, with 15 mmol of boronic derivative (chromatography eluent: petroleum ether/dichloromethane 3/7).

Yield: 2.79 g; 70%. A yellow powder is obtained.

$^1$H NMR (400 MHz, CDCl$_3$) δ 4.28-4.40 (m, 2H, H$_g$'); 4.37-4.40 (m, 2H, H$_f$); 6.48 (s, 1H, H$_h$); 7.86 (d, J=9.0 Hz, 2H, H$_c$); 8.17 (d, J=9.0 Hz, 2H, H$_b$).

$^{13}$C NMR (100 MHz, CDCl$_3$) δ 64.3 (OC$_g$H$_2$); 65.1 (OC$_f$H$_2$); 101.0 (C$_h$); 124.1 (C$_b$); 125.7 (C$_c$); 139.8 (C$_a$); 140.9 (C$_g$); 142.9 (C$_f$); 145.8 (C$_d$).

MS: M calculated 263; found: 263.

Elemental analysis: calculated: C 54.75, H 3.45, N 5.32, S 12.18; found: C 55.04, H 3.50, N 6.05, S 10.88.

2-(4-Nitrophenyl)-3,4,3',4'-bis(ethylenedioxy)-5,2'-bithiophene

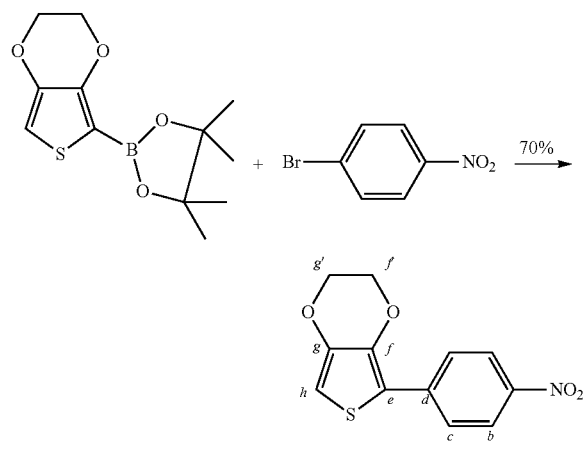

The compound nitrophenyl-bi-EDOT was prepared by the general procedure described above, with 2 mmol of boronic derivative. The product was purified by silica gel chromatography using a 3/7 petroleum ether/dichloromethane mixture as eluent.

Yield: 316.3 mg; 36%. A dark powder is obtained.

$^1$H NMR (400 MHz, CDCl$_3$) δ 4.23-4.27 (m, 2H, OCH$_2$); 4.36-4.40 (m, 6H, 3×OCH$_2$); 6.36 (s, 1H, H$_1$); 7.84 (d, J=9.2 Hz, 2H, H$_c$); 8.17 (d, J=9.2 Hz, 2H, H$_b$).

$^{13}$C NMR (100 MHz, CDCl$_3$) δ 63.9, 64.0, 64.4 and 64.7 (4×OCH$_2$); 98.6 (C$_l$); 108.8, 111.5, 111.7 (C$_e$, C$_h$ and C$_i$); 123.4 (C$_b$); 124.7 (C$_c$); 136.7, 137.4, 139.8, 140.7 (C$_f$, C$_g$, C$_j$, C$_k$); 139.3 (C$_a$); 144.4 (C$_b$); 145.0 (C$_d$).

MS C$_{18}$H$_{13}$NO$_6$NaS$_2$ [M+Na$^+$]: calculated: 426.0082, found: 426.0093.

Elemental analysis: calculated: C 53.59, H 3.25, N 3.47, S 15.89; found: C 54.74, H 3.54, N 3.60, S 14.02.

2-(4-Nitrophenyl)-3',4'-ethylenedioxy-5,2'-bithiophene

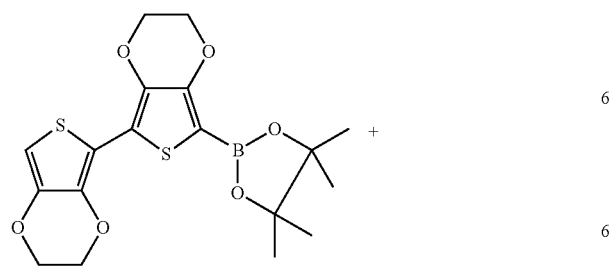

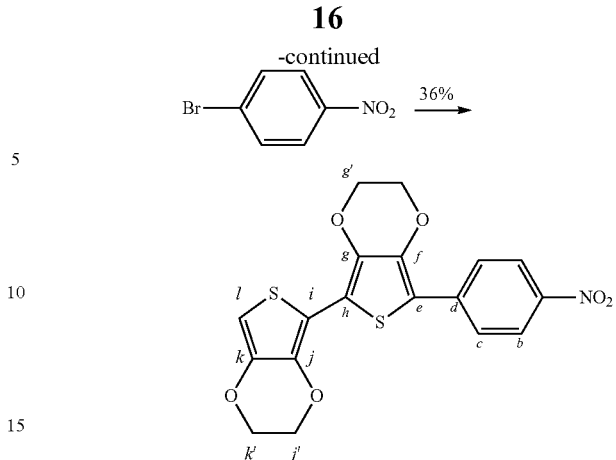

2-(4-Nitrophenyl)-3',4'-ethylenedioxy-5,2'-bithiophene was prepared according to the general procedure described above, starting from 4 mmol of boronic derivative (chromatography eluent: 25/75 petroleum ether/dichloromethane mixture).

Yield: 1.38 g; 78%. An orange powder is obtained.

$^1$H NMR (400 MHz, CDCl$_3$) δ 4.28-4.31 (m, 2H, OCH$_2$); 4.40-4.42 (m, 2H, OCH$_2$); 6.23 (s, 1H, H$_l$); 7.25 (d, J=4.0 Hz, 2H, H$_f$ or H$_g$); 7.41 (d, J=4.0 Hz, 2H, H$_f$ or H$_g$); 7.73 (d, J=8.8 Hz, 2H, H$_c$); 8.24 (d, J=8.8 Hz, 2H, H$_b$).

$^{13}$C NMR (100 MHz, CDCl$_3$) δ 64.6 and 65.2 (2×OCH$_2$); 98.1 (C$_l$); 111.7 and 138.4 (C$_j$ and C$_k$); 123.9 and 126.0 (C$_f$ and C$_g$); 124.5 (C$_b$); 125.4 (C$_c$); 137.6 and 139.0 (C$_h$ and C$_i$); 140.6 (C$_a$); 142.0 (C$_e$); 146.3 (C$_d$).

MS C$_{16}$H$_{11}$NO$_4$S$_2$ [M+H$^+$]: calculated: 345.0130, found: 345.0145.

Elemental analysis C$_{16}$H$_{11}$NO$_4$S$_2$: calculated: C 55.64, H 3.21, N 4.06, S 18.56; found: C 55.04, H 3.13, N 4.22, S 17.97.

2-(4-Nitrophenyl)-3,4-ethylenedioxy-5,2'-bithiophene

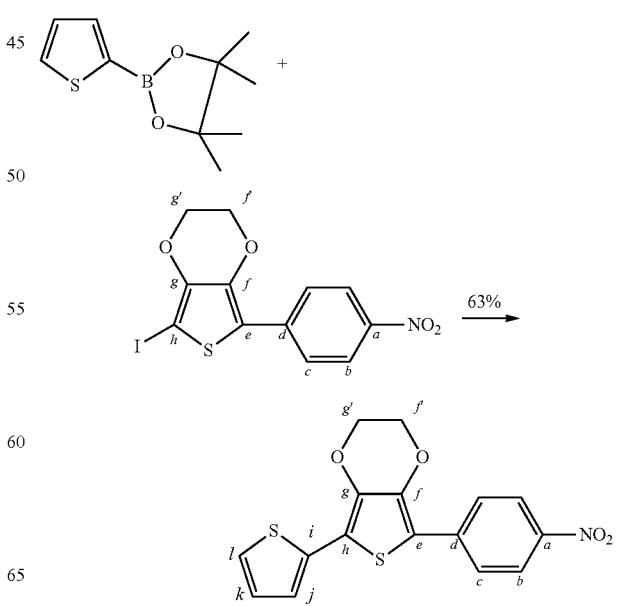

2-(4-Nitrophenyl)-3,4-ethylenedioxy-5,2'-bithiophene was prepared according to the general procedure described above for the Suzuki coupling reaction, with 2 mmol of boronic derivative (chromatography eluent: 25/75 petroleum ether/dichloromethane mixture).

Yield: 690 mg; 63%. An orange powder is obtained.

$^1$H NMR (400 MHz, CDCl$_3$) δ 4.43 (s, 4H, 2×OCH$_2$); 7.08 (dd, 1H, J=3.2 and 5.2 Hz, CH$_k$); 7.30 (d, 1H, J=5.2 Hz, CH$_l$); 7.34 (d, 1H, J=3.2 Hz, CH$_j$); 7.86 (d, 1H, J=8.8 Hz, CH$_c$); 8.18 (d, 1H, J=8.8 Hz, CH$_b$).

$^{13}$C NMR (100 MHz, CDCl$_3$) δ 64.7 and 65.0 (2×OCH$_2$); 112.1 (C$_e$); 113.8 (C$_i$); 124.0 (C$_j$); 124.1 (C$_b$); 125.0 (C$_l$); 125.6 (C$_c$); 127.4 (C$_k$); 133.9 (C$_h$); 137.9 and 140.9 (C$_f$ and C$_g$); 139.4 (C$_a$); 145.3 (C$_d$).

MS C$_{16}$H$_{11}$NO$_4$S$_2$ [M$^+$]: calculated: 345.0130, found: 345.0139.

Elemental analysis C$_{16}$H$_{11}$NO$_4$S$_2$: calculated: C 55.64, H 3.21, N 4.06, S 18.56; found: C 55.27, H 3.21, N 4.09, S 17.70.

2-(4-Nitrophenyl)-3,4,3',4',3'',4''-ter(ethylenedioxy)-5,2',5',2''-terthiophene

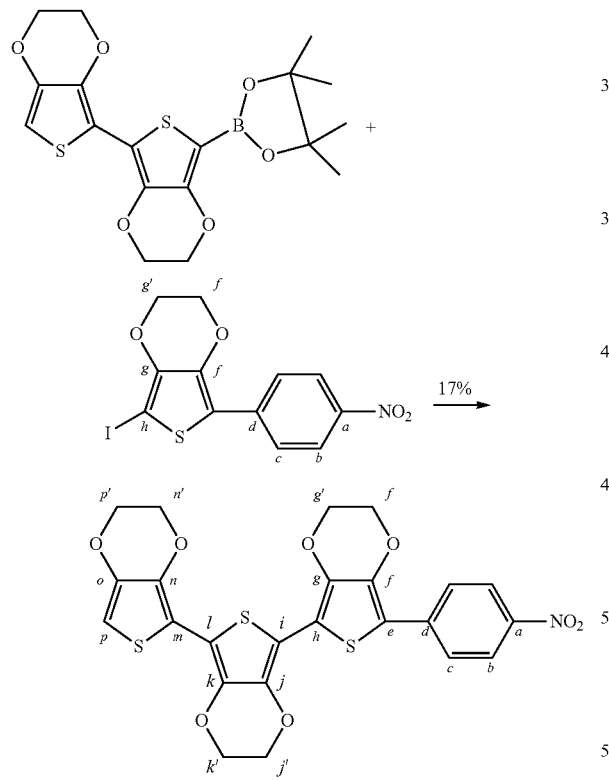

The nitrophenyl-terEDOT compound was prepared according to the general procedure described above for the Suzuki coupling reaction with 2 mmol of boronic derivative. The product was purified by alumina chromatography using dichloromethane as eluent.

Yield: 465 mg; 71%. A dark powder is obtained.

$^1$H NMR (400 MHz, CDCl$_3$) δ 4.26 (m, 2H, OCH$_2$); 4.30-4.50 (m, 10H, 5×OCH$_2$); 6.33 (s, 1H, CH$_p$); 7.86 (d, 2H, J=8.8 Hz, CR$_c$) 8.19 (d, 2H, J=8.8 Hz, CH$_b$).

MS C$_{24}$H$_{17}$NO$_8$S$_3$ [M+H$^+$]: calculated: 543.0116; found: 543.0126.

Example 4

General Procedure for the Reduction of the Nitro (NO$_2$) Functional Group to Give an Amine (NH$_2$) [5]

10% palladium-on-charcoal (0.086 mmol, 10%) and hydrazine (1 ml) are added to a solution of the nitro derivative (0.86 mmol) in THF (20 ml). The reaction mixture is brought to reflux for 4 hours. After cooling to ambient temperature (20° C.), the suspension is filtered through celite and then the solvent is evaporated under vacuum. The residue dissolves in dichloromethane, is washed with water and then the solution is dried over magnesium sulfate. The product is used without additional purification.

2-(4-Aminophenyl)-3,4,3',4'-bis(ethylenedioxy)-5,2'-bithiophene

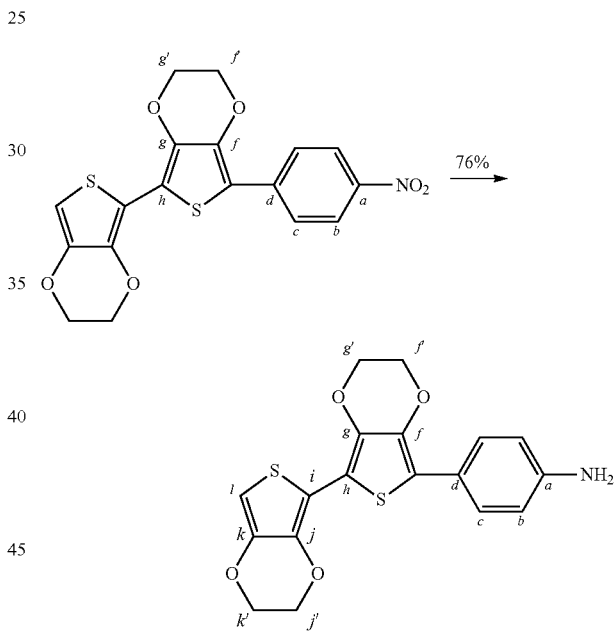

The amine derivative was prepared from 1 mmol of nitro derivative, according to the general procedure for reduction of the nitro functional group to give an amine indicated above.

Yield: 124 mg; 76%. A red powder is obtained.

$^1$H NMR (300 MHz, CDCl$_3$) δ 3.70-3.73 (broad s, 2H); 4.24-4.27 (m, 2H); 4.33-4.37 (m, 6H); 6.27 (s, 1H); 6.69 (d, 2H, J=8.4 Hz); 7.55 (d, 2H, J=8.4 Hz).

$^{13}$C NMR (75 MHz, CDCl$_3$) δ 64.6, 64.6, 64.9 and 65.0 (4×CH$_2$O); 97.3 (C$_1$H); 106.2 (C$_i$ or C$_h$); 110.2 (C$_i$ or C$_h$); 115.2 (C$_b$H); 115.8 (C$_e$); 123.7 (C$_a$); 127.3 (C$_c$H); 136.3, 136.7, 137.5 and 141.3 (C$_f$, C$_g$, C$_j$ and C$_k$); 145.0 (C$_d$).

MS C$_{18}$H$_{15}$NO$_4$NaS$_2$ [M+H$^+$]: calculated: 374.0521; found: 374.0515.

Elemental analysis C$_{12}$H$_{11}$NO$_2$S: calculated: C 57.89, H 4.05, N 3.75, S 17.17; found: C 58.50, H 4.33, N 3.93, S 15.95.

2-(4-Aminophenyl)-3',4'-ethylenedioxy-5,2'-bithiophene

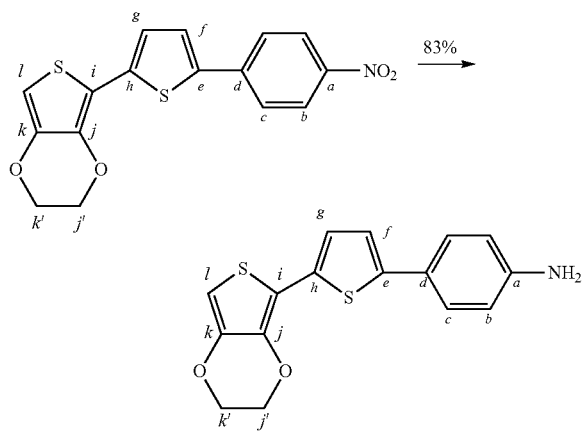

The amine derivative was prepared starting from 0.6 mmol of nitro derivative, according to the general procedure for the reduction of nitro functional group to give an amine indicated above.

Yield: 189 mg; 83%. A yellow powder is obtained.

$^1$H NMR (300 MHz, CDCl$_3$) δ 4.76 (s, 2H); 4.25-4.27 (m, 2H, H$_{j'}$); 4.34-4.37 (m, 2H, H$_{k'}$); 6.20 (s, 1H, H$_1$); 6.68 (d, 2H, J=8.8 Hz, H$_b$); 7.06 (d, 1H, J=4.0 Hz, H$_f$); 7.14 (d, 1H, J=4.0 Hz, H$_g$); 7.41 (d, 2H, J=8.8 Hz, H$_c$).

$^{13}$C NMR (75 MHz, CDCl$_3$) δ 64.6 (OC$_{j'}$H$_2$); 65.0 (C$_{k'}$H$_2$); 96.5 (C$_l$); 112.6 (C$_i$); 115.3 (C$_b$); 121.3 (C$_f$); 123.8 (C$_g$); 125.0 (C$_a$); 126.8 (C$_c$); 132.4 (C$_h$); 137.2 (C$_k$); 141.9 (C$_j$); 143.2 (C$_e$); 145.9 (C$_d$).

MS C$_{16}$H$_9$NO$_2$S$_2$ [M+H$^+$]: calculated: 316.0466; found: 316.0461.

Elemental analysis C$_{16}$H$_9$NO$_2$S$_2$: calculated: C 60.93, H 4.15, N 4.44, S 20.33; found: C 60.82, H 4.80, N 4.01, S 17.46.

2-(4-Aminophenyl)-3,4-ethylenedioxy-5,2'-bithiophene

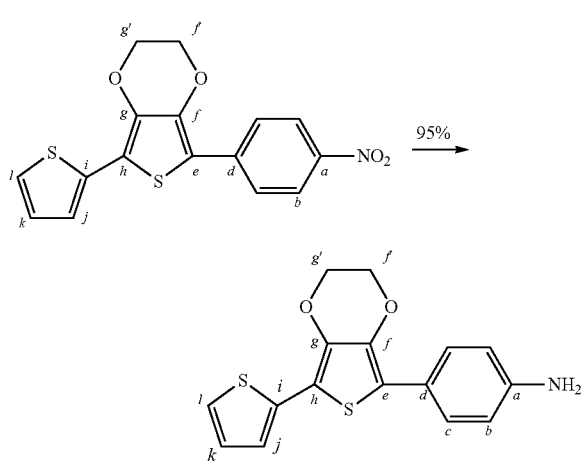

The amine derivative was prepared starting from 0.86 mmol of nitro derivative, according to the general procedure for the reduction of the nitro functional group to give an amine indicated above.

Yield: 270 mg; 95%. A yellow powder is obtained.

$^1$H NMR (300 MHz, CDCl$_3$) δ 4.32-4.35 (m, 2H); 4.37-4.39 (m, 2H); 6.70 (d, 2H, J=8.8 Hz, H$_b$); 7.02 (dd, 1H, J=3.6 and 5.0 Hz, H$_k$); 7.20 (d, 1H, J=5.0 Hz, H$_l$); 7.22 (d, 1H, J=3.6 Hz, H$_j$); 7.53 (d, 2H, J=8.8 Hz, H$_c$).

$^{13}$C NMR (75 MHz, CDCl$_3$) δ 64.6 and 64.9 (2×OCH$_2$); 108.3 (C$_e$ or C$_h$); 115.2 (C$_b$); 115.5 (C$_a$); 122.3 (C$_j$); 123.3 (C$_l$); 127.1 (C$_k$); 127.3 (C$_c$); 135.0 (C$_i$); 136.7 (C$_f$ or C$_g$); 137.9 (C$_f$ or C$_g$); 145.3 (C$_d$).

MS C$_{16}$H$_9$NO$_2$S$_2$ [M+H$^+$]: calculated: 316.0466; found: 316.0466.

Elemental analysis C$_{16}$H$_9$NO$_2$S$_2$: calculated: C 60.93, H 4.15, N 4.44, S 20.33; found: C 61.11, H 4.61, N 4.62, S 17.95.

2-(4-Aminophenyl)-3,4,3',4',3'',4''-ter(ethylenedioxy)-5,2',5',2''-terthiophene

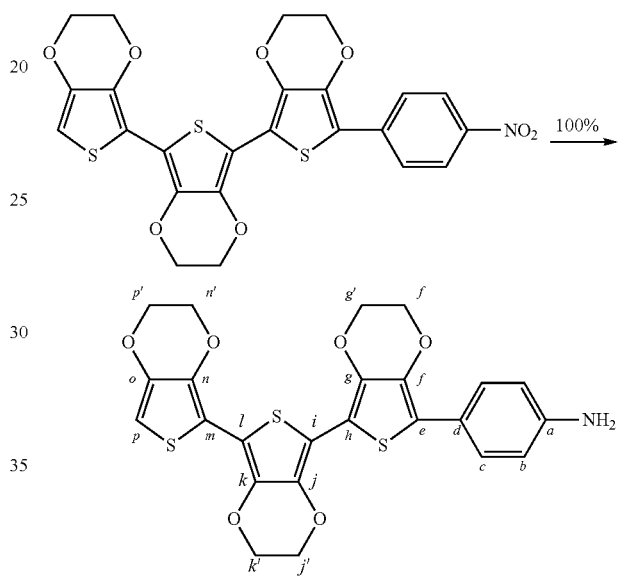

The amine derivative was prepared starting from 0.11 mmol of nitro derivative, according to the general procedure for the reduction of the nitro functional group to give an amine indicated above.

Yield: 56 mg; quantitative. A red powder is obtained.

$^1$H NMR (300 MHz, CDCl$_3$) δ 4.21-4.40 (m, 12H); 6.27 (s, 1H, CH$_p$); 6.68 (d, 2H, J=7.6 Hz, CH$_b$); 7.55 (d, 2H, J=7.6 Hz, CH$_c$).

MS: C$_{24}$H$_{19}$NO$_6$S$_3$ [M+H$^+$]: calculated: 513.0374; found: 513.0371.

Example 5

Process for the Preparation of 2-(4-nitrophenyl)-3,4,3',4'-bis(ethylenedioxy)-5,2'-bithiophene [6]

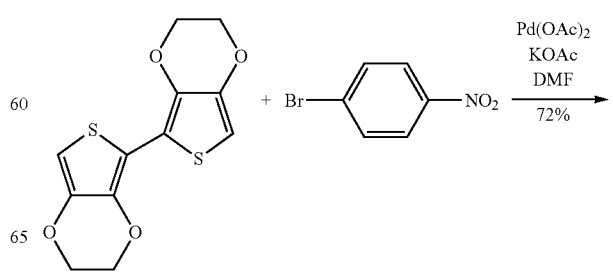

-continued

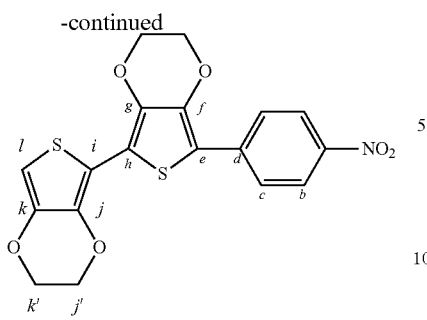

BiEDOT (2.2 g, 7.8 mmol, 1.3 eq.), 4-bromonitrobenzene (1.21 g, 6 mmol) and potassium acetate (1.76 g, 18 mmol, 3 eq.) are successively introduced into a Schlenk flask containing 20 ml of DMF. After complete dissolution of the reactants, palladium acetate (134 mg, 0.6 mmol, 0.1 eq.) is added and then the reaction medium is heated at 80° C. for one hour. After returning to ambient temperature (20° C.), the red precipitate is filtered off and washed with ethanol. The nitrated compound is subsequently used without additional purification.

Yield: 72%.

LIST OF REFERENCES

[1] U.S. Pat. No. 6,130,339
[2] U.S. Pat. No. 6,197,921 B1
[3] G. A. Sotzing, J. R. Reynolds, P. J. Steel, Adv. Mater., 1997, 9, 10, 795-798.
[4] M. Frigoli, C. Mostrou, A. Samat, R. Guglielmetti, *Eur. J. Org. Chem.*, 2003, 2799-2812.
[5] L. Flamigni, B. Venture, E. Baranooff, J-P. Collin, J-P. Sauvage, *Eur. J. of Inorg. Chem.*, 2007, 33, 5189-5198.
[6] A. Borghese, G. Geldhof, L. Antoine, i Tetrahedron, 2006, 47, 9249-9252.

What is claimed is:

1. A compound of formula (I):

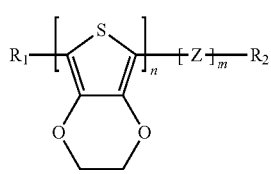

wherein:
$R_1$ represents a hydrogen atom, a halogen atom, a hydroxyl group, a $C_1$-$C_4$ alkoxy group, a —$COOR_3$ group, a —$COR_3$ group, an —$SR_3$ group, an —$SeR_3$ group, an —$Si(OR_3)$ group, an —$NR_3R_4$ group, a —C≡N group, an —$N_3$ group, a —C≡C—H group, a heterocycle chosen from the group consisting of pyrrole, furan, phosphole, thiophene, tetrathiafulvalene, selenophene, imidazole, oxazole, thiazole, triazole, pyrazole, pyridine, bipyridine, terpyridine, phenanthroline, pyrazine, pyridazine and pyrimidine, ferrocene, cobaltocene, a polyethylene group of formula —(—O—$CH_2$—$CH_2$—$)_p$—, a $C_1$-$C_{10}$ alkyl group and a phenyl group, said polyethylene, alkyl, phenyl and heterocycle groups being optionally substituted by one or more groups chosen from the group consisting of:
a —$COOR_3$ group, a —$COR_3$ group, a hydroxyl group, a $C_1$-$C_4$ alkoxy group and a —$CONR_3R_4$ group;
$R_2$ represents an amino (—$NH_2$) group, a diazo ($N_2^+$) group, an aniline group, a phenyl group substituted by a diazo ($N_2^+$) group;
Z represents thiophene, optionally substituted by one or more groups chosen from the group consisting of:
a $C_1$-$C_{10}$ alkyl group, a carboxyl group, a —$COOR_3$ group, a hydroxyl group or a $C_1$-$C_4$ alkoxy group;
$R_3$ and $R_4$ represent, independently of one another, a hydrogen atom, a $C_1$-$C_6$ alkyl group or a phenyl group;
n=1, 2, 3, 4 or 5;
m=0, 1, 2 or 3; and
p=0, 1, 2, 3, 4 or 5.

2. The compound of formula (I) as claimed in claim 1, in which:
$R_1$ represents a hydrogen atom or thiophene;
$R_2$ represents the amino (—$NH_2$) group or the aniline group;
Z represents thiophene;
n=1, 2 or 3;
m=0 or 1;
wherein, when $R_1$ represents a hydrogen atom and m=0, then n is other than 1.

3. The compound of formula (I) as claimed in claim 1, in which:
$R_1$ represents a hydrogen atom or thiophene;
$R_2$ represents the aniline group or the phenyl group substituted by the diazo ($N_2^+$) group;
Z represents thiophene;
n=1, 2 or 3;
m=0 or 1.

4. The compound of formula (I) as claimed in claim 3, wherein, when m=0, n is other than 1.

5. The compound of formula (I) as claimed in claim 1, wherein:
$R_1$ represents a hydrogen atom;
$R_2$ represents the aniline group;
n=2; and
m=0.

6. The compound of formula (I) as claimed in claim 1, wherein:
$R_1$ represents thiophene;
$R_2$ represents the aniline group;
n=1; and
m=0.

7. The compound of formula (I) as claimed in claim 1, wherein:
$R_1$ represents a hydrogen atom;
$R_2$ represents the aniline group;
Z represents thiophene;
n=1; and
m=1.

8. The compound of formula (I) as claimed in claim 1, wherein:
$R_1$ represents a hydrogen atom;
$R_2$ represents the aniline group;
n=3; and
m=0.

9. A process for preparing a compound of formula (I) as claimed in claim 1, comprising the step of:
reacting a halogenated compound of formula (II) with a compound of formula (III) in the presence of at least one palladium catalyst for obtaining the compound of formula (I):

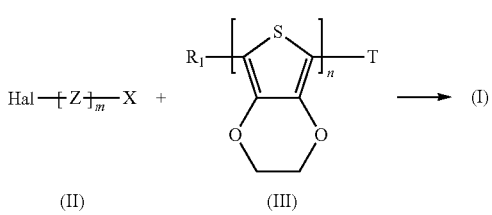

wherein Z, $R_1$, n and m are as defined in claim 1;
Hal represents a halogen atom;
T represents a hydrogen atom or a —B(OR')(OR") group, in which:
  R' and R" represent, independently of one another, a hydrogen atom, a $C_1$-$C_6$ alkyl group or an aryl group chosen from the group consisting of benzyl, phenyl, tolyl and xylyl, or
  R' and R" together form a 5- or 6-membered ring optionally substituted by one or more $C_1$-$C_4$ alkyl groups;
X represents an —$NO_2$ group or a phenyl group substituted by an —$NO_2$ group.

10. A process for preparing a compound of formula (I) as claimed in claim 1, comprising the step of:
  reacting a halogenated compound of formula (II) with a compound of formula (III) in the presence of at least one palladium catalyst for obtaining the compound of formula (IV), wherein compound (IV) provides the compound (I) after reduction, and formulas II, III, and IV are:

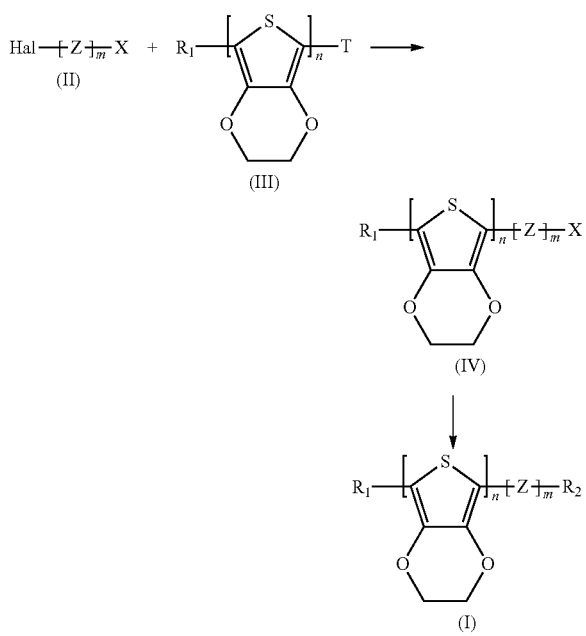

with Z, $R_1$, n and m as defined above;
Hal represents a halogen atom;
T represents a hydrogen atom or a —B(OR')(OR") group, in which:
  R' and R" represent, independently of one another, a hydrogen atom, a $C_1$-$C_6$ alkyl group or an aryl group chosen from the group consisting of benzyl, phenyl, tolyl and xylyl, or
  R' and R" together form a 5- or 6-membered ring optionally substituted by one or more $C_1$-$C_4$ alkyl groups;

X represents an —$NO_2$ group or a phenyl group substituted by an —$NO_2$ group, it being understood that, when X is the —$NO_2$ group, $R_2$ represents an amino (—$NH_2$) group and, when X is the phenyl group substituted by an —$NO_2$ group, $R_2$ represents an aniline group.

11. A method for producing a layer on a substrate of insulating, semi-conducting or conducting surfaces, with a compound of formula (I) as claimed in claim 1, comprising the step of:
  grafting the compound to form the layer adhered on the substrate.

12. A method of producing a device, comprising adhering a layer of a compound of formula (I) as claimed in claim 1, and forming electrical connections to the layer to produce the device, configured to act as at least one of an organic light-emitting diode, an organic shotovoltaic cell an organic transistor a single-electron transistor, a surface having switchable wetting properties, a sensor, and a biosensor.

13. A method of producing a device, comprising providing a substrate, and adhering a coating of a compound of formula (I) as claimed in 1, on the substrate, to form a covalently grafted layer, resulting in at least one of a corrosion-resistant coating, a transparent electrode, a self-lubricating surface, an electrochromic coating, an intelligent coating and an adhesion primer.

14. A method of storm energy, comprisin fg orming a device having at least one electrode formed using a compound of formula (I) as claimed in claim 1, and passing an electrical current through the at least one electrode to store energy in the device, said device being configured to act as at least one of a battery and a supercapacitor.

15. A material comprising a compound of formula (I) as defined in claim 1.

16. An article comprising a compound of formula (I) as defined in claim 1.

17. A method of using a compound of formula (I) as claimed in claim 1 in the field of the storage of energy comprising the step of:
  depositing the compound on carbon nanotubes to form an electrode material for batteries or supercapacitors.

18. An article formed from the compound of formula (I) of claim 1, wherein $R_2$ represents an amino (—$NH_2$) group or an aniline (—$C_6H_4NH_2$) group formed by reduction of a corresponding —$NO_2$ group or a phenyl group substituted by an —$NO_2$ group,
  the article comprising a layer of the compound grafted on a substrate through a further reduction of the compound to form a covalent linkage.

19. A grafted layer adhered through a covalent bond to a substrate, formed by the reduction of a compound of formula (I):

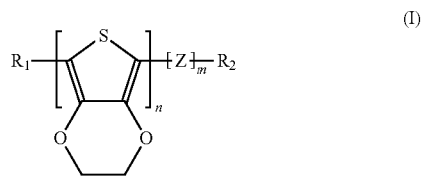

wherein:
$R_1$ represents a hydrogen atom, a halogen atom, a hydroxyl group, a $C_1$-$C_4$ alkoxy group, a —$COOR_3$ group, a —$COR_3$ group, an —$SR_3$ group, an —$SeR_3$ group, an —$Si(OR_3)$ group, an —$NR_3R_4$ group, a —C≡N group, an —$N_3$ group, a —C≡C—H group, a heterocycle chosen from the group consisting of pyrrole, furan, phosphole, thiophene, tetrathiafulvalene, selenophene, imidazole, oxazole, thiazole, triazole, pyrazole, pyridine, bipyridine, terpyridine, phenanthroline, pyrazine, pyridazine and pyrimidine, ferrocene, cobaltocene, a polyethylene group of formula —(—O—CH$_2$—CH$_2$—)$_p$—, a C$_1$-C$_{10}$ alkyl group and a phenyl group, said polyethylene, alkyl, phenyl and heterocycle groups being optionally substituted by one or more groups chosen from the group consisting of:
- a —COOR$_3$ group, a —COR$_3$ group, a hydroxyl group, a C$_1$—C$_4$ alkoxy group and a —CONR$_3$R$_4$ group;

R$_2$ represents an amino (—NH$_2$) group, a diazo (N$_2^+$) group, an aniline group, a phenyl group substituted by a diazo (N$_2^+$) group, an —NO$_2$ group or a phenyl group substituted by an —NO$_2$ group;

Z represents thiophene, optionally substituted by one or more groups chosen from the group consisting of:
- a C$_1$-C$_{10}$ alkyl group, a carboxyl group, a —COOR$_3$ group, a hydroxyl group or a C$_1$-C$_4$ alkoxy group;

R$_3$ and R$_4$ represent, independently of one another, a hydrogen atom, a C$_1$-C$_6$ alkyl group or a phenyl group;

n=1, 2, 3, 4 or 5;
m=0, 1, 2 or 3;
p=0, 1, 2, 3, 4 or 5;
wherein, when R$_1$ represents a hydrogen atom and m=0, then n is other than 1.

20. The grafted layer according to claim 19, wherein R$_2$ represents an —NO$_2$ group or a phenyl group substituted by an —NO$_2$ group.

21. The grafted layer according to claim 19, wherein:
R$_1$ represents a hydrogen atom;
n=2 or 3; and
m=0.

22. The grafted layer according to claim 19, wherein:
R$_1$ represents thiophene;
n=1; and
m=0.

23. The grafted layer according to claim 19, wherein:
R$_1$ represents a hydrogen atom;
Z represents thiophene;
n=1; and
m=1.

* * * * *